(12) United States Patent
Martin et al.

(10) Patent No.: US 10,339,464 B2
(45) Date of Patent: Jul. 2, 2019

(54) SYSTEMS AND METHODS FOR GENERATING BIOMARKER SIGNATURES WITH INTEGRATED BIAS CORRECTION AND CLASS PREDICTION

(71) Applicant: Philip Morris Products S.A., Neuchatel (CH)

(72) Inventors: Florian Martin, Peseux (CH); Yang Xiang, Neuchatel (CH)

(73) Assignee: Philip Morris Products S.A., Neuchatel (CH)

( * ) Notice: Subject to any disclaimer, the term of this patent is extended or adjusted under 35 U.S.C. 154(b) by 862 days.

(21) Appl. No.: 14/409,681

(22) PCT Filed: Jun. 21, 2013

(86) PCT No.: PCT/EP2013/062980
§ 371 (c)(1),
(2) Date: Dec. 19, 2014

(87) PCT Pub. No.: WO2013/190084
PCT Pub. Date: Dec. 27, 2013

(65) Prior Publication Data
US 2015/0178639 A1    Jun. 25, 2015

Related U.S. Application Data

(60) Provisional application No. 61/662,792, filed on Jun. 21, 2012.

(51) Int. Cl.
*G06N 20/00* (2019.01)
*G06F 16/28* (2019.01)
*G06F 19/24* (2011.01)

(52) U.S. Cl.
CPC ........... *G06N 20/00* (2019.01); *G06F 16/285* (2019.01); *G06F 19/24* (2013.01)

(58) Field of Classification Search
CPC ............ G06N 5/04; G06N 7/005; G06N 5/02; G06N 99/005; G06N 20/00;
(Continued)

(56) References Cited

U.S. PATENT DOCUMENTS 7,761,239 B2 * 7/2010 Chen ...................... G06F 19/24
702/19
2005/0086035 A1    4/2005 Peccoud et al.
(Continued)

FOREIGN PATENT DOCUMENTS

CN         1749988 A     3/2006
CN       101944122 A     1/2011
(Continued)

OTHER PUBLICATIONS

"Diagnosis of multiple cancer types by shrunken centroids of gene expression", Tibshirani, R., et al., Proceedings of the National Academy of Sciences—PNAS, National Academy of Sciences, US, vol. 99, No. 10, May 14, 2002, pp. 6567-6572.
(Continued)

*Primary Examiner* — Robert A Cassity
*Assistant Examiner* — Peter D Coughlan
(74) *Attorney, Agent, or Firm* — Sterne, Kassler Goldstein & Fox P.L.L.C.

(57) ABSTRACT

Described herein are systems and methods for correcting a data set and classifying the data set in an integrated manner. A training data set, a training class set, and a test data set are received. A first classifier is generated for the training data set by applying a machine learning technique to the training data set and the training class set, and a first test class set is generated by classifying the elements in the test data set according to the first classifier. For each of multiple iterations, the training data set is transformed, the test data set is transformed, and a second classifier is generated by applying (Continued)

a machine learning technique to the transformed training data set. A second test class set is generated according to the second classifier, and the first test class set is compared to the second test class set.

22 Claims, 6 Drawing Sheets

(58) Field of Classification Search
CPC . G06F 17/30598; G06F 19/24; C12Q 1/6886; C12Q 1/6883
See application file for complete search history.

(56) References Cited

U.S. PATENT DOCUMENTS

| | | | |
|---|---|---|---|
| 2006/0074826 A1 | 4/2006 | Heumann et al. | |
| 2006/0177827 A1 | 8/2006 | Dejori et al. | |
| 2007/0198653 A1 | 8/2007 | Jarnagin et al. | |
| 2009/0300417 A1* | 12/2009 | Bonissone | G05B 23/0254 714/26 |
| 2009/0326897 A1 | 12/2009 | Schuppert et al. | |
| 2010/0086501 A1 | 4/2010 | Chang et al. | |
| 2010/0216660 A1 | 8/2010 | Nikolsky et al. | |
| 2011/0190657 A1 | 8/2011 | Zhou et al. | |
| 2012/0054184 A1* | 3/2012 | Masud | G06F 17/30598 707/737 |
| 2012/0143805 A1 | 6/2012 | Gold et al. | |
| 2013/0262465 A1* | 10/2013 | Galle | G06F 17/30 707/737 |
| 2014/0214336 A1 | 7/2014 | Martin et al. | |
| 2015/0154353 A1 | 6/2015 | Martin et al. | |
| 2015/0220838 A1 | 8/2015 | Martin et al. | |

FOREIGN PATENT DOCUMENTS

| | | |
|---|---|---|
| CN | 102135979 A | 7/2011 |
| CN | 102214213 A | 10/2011 |
| JP | 2008-520396 A | 6/2008 |
| JP | 2009-075737 A | 4/2009 |
| JP | 2012-501183 A | 1/2012 |
| WO | WO 2005052181 | 6/2005 |
| WO | WO 2006-058176 A1 | 6/2006 |
| WO | WO 2011005893 | 1/2011 |
| WO | WO 2013034300 | 3/2013 |
| WO | WO 2013190083 | 12/2013 |
| WO | WO 2013190084 | 12/2013 |
| WO | WO 2013190085 | 12/2013 |

OTHER PUBLICATIONS

"The stability of feature selection and class prediction from ensemble tree classifiers", Paul, Jerome et al., Proceedings of the European Symposium on Artificial Neural Networks, Computational Intelligence and Machine Learning 2012, Apr. 27, 2012 pp. 263-268.
"Mean—Adjusted bootstrap for two—Phase Samplling", Saigo, Hiroshi, Survey Methodology, Jun. 1, 2007, retrieved from the Internet: URL:http://www.statcan.gc.ca/ads-annonces/12-001-x/9853-eng.pdf (retrieved on Oct. 29, 2013).
"Bayesian integrated functional analysis of microarray data", Bhattacharjee, M., et al., Bioinformatics, vol. 20, No. 17, Jun. 4, 2004 pp. 2943-2953.
"Prediction of cancer outcome with microarrays: a multiple random validation strategy", Michiels, S., et al, The Lancet, Lancet Limited, London GB, vol. 365, No. 9458, Feb. 5, 2005, pp. 488-492.
International Search Report and Written Opinion dated Nov. 27, 2013 in International Application No. PCT/EP2013/062980.
Burgoon et al., "Automated quantitative dose-response modeling and point of departure determination for large toxicogenomic and high-throughput screening data sets," Toxicol Sci., 104:412-418 (2008).
Ekins et al., "Techniques: application of systems biology to absorption, distribution, metabolism, excretion and toxic," Trends Pharmacol Sci., 26:202-209 (2005).
Marchal et al., Computational Biology and Toxicogenomics, Chapter 3 of Predictive Toxicology (ed. Helma, C.) 37-92 (2005).
Kim et al., "Can markov chain models mimix biological regulation?" Journal of Biological System, 10:337-357 (2002).
Nie et al., "Predictive toxicogenomics approaches reveal underlying molecular mechanisms of nongenotoxic carcinogenicity," Mol Carcinog., 45:914-933 (2006).
Toyoshiba et al., "Gene interaction network suggests dioxin induces a significant linkage between aryl hydrocarbon receptor and retinoic acid receptor beta," Environ Health Perspect., 112:1217-1224 (2004).
U.S. Appl. No. 14/342,689 Non-Final Office Action dated Apr. 22, 2016.
Blum et al., "Combining labeled and unlabeled data with co-training", Proceedings of the 11th Annual Conference on Computational Learning Theory. Colt '98, Madison, WI, Jul. 24-26, 1998 (Annual Conference on Computational Learning Theory), New York, NY, pp. 92-100.
Chung, "Chapter 1: Eigenvalues and the laplacian of a graph," Spectral Graph Theory, American Mathematical Society, Providence, pp. 1-22 (1997).
Glez-Pena et al., "A simulated annealing-based algorithm for iterative class discovery using fuzzy logic for informative gene selection", Journal of Integrated Omics, 1:66-77 (2011).
Haggarty et al., "Chemical genomic profiling of biological networks using graph theory and combinations of small molecule perrturbations," J Am Chem Soc., 125:10543-10545 (2003).
Heb et al., "Iterative Ensemble Classification for Relational Data: A Case Study of Semantic Web Services", ECML 2004, LNAI 3201, Jan. 1, 2004, pp. 156-167, retrieved from the Internet: URL:http://citeseerx.ist.psu.edu/viewdoc/download?doi=10.1.1.3.658&rep=rep1&type=pdf (retrieved on Oct. 22, 2013).
Hoeng et al., "A network-based approach to quantifying the impact of biologically active substances", Drug Discovery Today, 17: 413-418 (2012).
International Search Report and Written Opinion dated Nov. 13, 2013 in International Application No. PCT/EP2013/062982.
International Search Report dated Jul. 25, 2013 and Written Opinion dated Mar. 12, 2014 in International Application No. PCT/EP2012/003760.
International Search Report dated Oct. 11, 2013 and Written Opinion dated Dec. 23, 2014 in International Application No. PCT/EP2013/062979.
Kirkpatrick et al., "Optimization by simulated annealing", Science, American Association for the Advancement of Science, Washington, D.C., 2:671-680 (1983).
Lee et al., "Analysis of AML genes in dysregularted molecular networks," BMC Bioinformatics, 10:S2 (2009).
Lim et al., "Master regulartors used as breast cancer metastasis classifier", Pac symp Biocomput., Jan. 1, 2009, pp. 504-515, retrieved from the Internet: URL:http://www.ncbi.mlm.nih.gov/pmc/articles/PMC2740937/pdf/nihms106219.pdf (retrieved on Sep. 12, 2013).
Lin et al., "Parmeter determination of support vector machine and feature selection using simulated annealing approach", Applied Soft Computing, 8:1568-4946 (2008).
Martin et al., "Assessment of network perturbation amplitudes by applying high-throughput data to causal biological networks", BMC Systems Biology, Biomed Central Ltd, 6:54-71 (2012).
Selventa—"Reverse Causal Reasoning Methods—White Paper", Anonymous, Retrieved from the Internet: URL:http://www.selventa.com/attachments/white_papers/reverse-causal-reasoning.pdf (retrieved on Aug. 17, 2012).
Tegner et al., "Perturbation to uncover gene networks," Trends in Genetics, 23:34-41 (2006).
Weston et al., "Feature selection for SVM's", Advances in Neural Information Processing Systems 13, pp. 668-674, retrieved from the Internet: URL:http://www0.cs.ucl.ac.uk/staff/M. Pontil/reading/featsel.pdf (retrieved on Jun. 13, 2013).

(56) References Cited

OTHER PUBLICATIONS

Westra et al., "Construction of a computable cell proliferation network focused on non-diseased lung cells", MBC Systems Biology, 5:105 (2011) (16 pages).

Yamanishi et al., " Extraction of correlated gene clusters from multiple genomic data by generalized kernel cannical correlation analysis," Bioinformatcs, 19:i323-i330 (2003).

Yang et al., "A Review of Ensemble Methods in Bioinformatics", Current Bioinformatics, 5:296-308 (2010).

Dietterich, "Ensemble methods in machine learning," International workshop on multiple classifier systems, Springer Berlin Heidelberg, 2000.

Huang et al., "Characterising and predicting haploinsufficiency in the human genome," PLoS Genet 6, 10:e1001154 (2010).

Liu, Kunhong, "Applications of multiple classifier ensemble system in gene microarray data analysis," China doctoral Thesis Full-Text Database Information Technologu Series, 2009(6): 1140-10 (2009) (Chinese language).

International Preliminary Report on Patentability directed to related International Patent Application No. PCT/EP2013/062980, dated Dec. 23, 2014; 8 pages.

Breiman; "Random Forests", *Machine Learning*; 2001; vol. 45; pp. 5-32; Kluwer Academic Publishers; Dordrecht, The Netherlands.

Bishop; *Neural Networks for Pattern Recognition*; 1995; Clarendon Press; Oxford, United Kingdom.

Tibshirani et al.; "Diagnosis of multiple cancer types by shrunken centroids of gene expression"; *Proceedings of the National Academy of Sciences of the United States of America*; 2002; vol. 99, issue 10; National Academy of Sciences; Washington, DC.

Nguyen et al.; "A supervised learning approach for imbalanced data sets"; *19th International Conference on Pattern Recognition*; Dec. 2008; pp. 1-4; Institute of Electrical and Electronics Engineers; Piscataway, NJ.

English-language abstract for Japanese Patent Application Publication No. 2009-075737 A, published Apr. 9, 2009; 1 page.

English-language abstract for Chinese Patent Application Publication No. 101944122 A, published Jan. 12, 2011; 1 page.

English-language abstract for Chinese Patent Application Publication No. 102135979 A, published Jul. 27, 2011; 1 page.

English-language abstract for Chinese Patent Application Publication No. 102214213 A, published Oct. 12, 2011; 1 page.

\* cited by examiner

SYSTEMS AND METHODS FOR GENERATING BIOMARKER SIGNATURES WITH INTEGRATED BIAS CORRECTION AND CLASS PREDICTION

CROSS REFERENCE TO RELATED APPLICATIONS

This application is a U.S. Nationalization of PCT Application No. PCT/EP2013/062980 filed Jun. 21, 2013, which claims the benefit of U.S. Provisional Application No. 61/662,792, filed Jun. 21, 2012, the entireties of which are incorporated herein by reference.

BACKGROUND

In the biomedical field it is important to identify substances that are indicative of a specific biological state, namely biomarkers. As new technologies of genomics and proteomics emerge, biomarkers are becoming more and more important in biological discovery, drug development and health care. Biomarkers are not only useful for diagnosis and prognosis of many diseases, but also for understanding the basis for development of therapeutics. Successful and effective identification of biomarkers can accelerate the new drug development process. With the combination of therapeutics with diagnostics and prognosis, biomarker identification will also enhance the quality of current medical treatments, thus play an important role in the use of pharmacogenetics, pharmacogenomics and pharmacoproteomics.

Genomic and proteomic analysis, including high throughput screening, supplies a wealth of information regarding the numbers and forms of proteins expressed in a cell and provides the potential to identify for each cell, a profile of expressed proteins characteristic of a particular cell state. In certain cases, this cell state may be characteristic of an abnormal physiological response associated with a disease. Consequently, identifying and comparing a cell state from a patient with a disease to that of a corresponding cell from a normal patient can provide opportunities to diagnose and treat diseases.

These high throughput screening techniques provide large data sets of gene expression information. Researchers have attempted to develop methods for organizing these data sets into patterns that are reproducibly diagnostic for diverse populations of individuals. One approach has been to pool data from multiple sources to form a combined data set and then to divide the data set into a discovery/training set and a test/validation set. However, both transcription profiling data and protein expression profiling data are often characterized by a large number of variables relative to the available number of samples.

Observed differences between expression profiles of specimens from groups of patients or controls are typically overshadowed by several factors, including biological variability or unknown sub-phenotypes within the disease or control populations, site-specific biases due to difference in study protocols, specimens handling, biases due to differences in instrument conditions (e.g., chip batches, etc), and variations due to measurement error. Some techniques attempt to correct to for bias in the data samples (which may result from, for example, having more of one class of sample represented in the data set than another class).

Several computer-based methods have been developed to find a set of features (markers) that best explain the difference between the disease and control samples. Some early methods included statistical tests such as LIMMA, the FDA approved mammaprint technique for identifying biomarkers relating to breast cancer, logistical regression techniques and machine learning methods such as support vector machines (SVM). Generally, from a machine learning perspective, the selection of biomarkers is typically a feature selection problem for a classification task. However, these early solutions faced several disadvantages. The signatures generated by these techniques were often not reproducible because the inclusion and exclusion of subjects can lead to different signatures. These early solutions also generated many false positive signatures and were not robust because they operated on datasets having small sample sizes and high dimensions.

Accordingly there is a need for improved techniques for identifying biomarkers for clinical diagnosis and/or prognosis, and more generally, for identifying data markers that can be used to classify elements in a data set into two or more classes.

SUMMARY

Applicants have recognized that existing computer-based methods disadvantageously apply bias correction techniques separately from class prediction techniques. The computer systems and computer program products described herein implement methods that apply an integrated approach to bias correction and class prediction, which may achieve improved classification performance in biomarker and other data classification applications. In particular, the computer-implemented methods disclosed herein adopt an iterative approach to bias correction and class prediction. In various embodiments of the computer-implemented methods, at least one processor in the system receives a training data set and a training class set, the training class set identifying a class associated with each of the elements in the training data set. The processor in the system also receives a test data set. The processor generates a first classifier for the training data set by applying a machine learning technique to the training data set and the training class set, and generates a first test class set by classifying the elements in the test data set according to the first classifier. For each of multiple iterations, the processor: transforms the training data set based on at least one of the training class set and the test class set, transforms the test data set by applying the transformation of the previous step, generates a second classifier for the transformed training data set by applying a machine learning technique to the transformed training data set and the training class set, and generates a second test class set by classifying the elements in the transformed test data set according to the second classifier. The processor also compares the first test class set to the second test class set, and when the first test class set and the second test class set differ, the processor stores the second class set as the first class set, stores the transformed test data set as the test data set and returns to the beginning of the iteration. The computer systems of the invention comprises means for implementing the methods and its various embodiments as described above.

In certain embodiments of the methods described above, the method further comprises outputting the second class set when the first test class set and the second test class set do not differ. In particular, the iterations as described above may be repeated until the first test class set and the second test class set converge, and there is no difference between the predicted classifications. In certain embodiments of the methods described above, an element of the training data set represents gene expression data for a patient with a disease, for a patient resistant to the disease, or for a patient without the disease. The elements of the training class set may correspond to known class identifiers for the data samples in the training data set. For example, the class identifiers may include categories such as "Disease Positive," "Disease Immune," or "Disease Free."

In certain embodiments of the methods described above, the training data set and the test data set are generated by randomly assigning samples in an aggregate data set to the training data set or the test data set. Randomly splitting the aggregate data set into the training data set and the test data set may be desirable for predicting classes and generating robust gene signatures. Furthermore, samples of the aggregate data set may be discarded prior to the splitting, or samples of the training data set or the test data set may be discarded after the splitting. In certain embodiments of the methods described above, the step of transforming the training data set, transforming the test data set, or both steps of transforming the training data set and transforming the test data set comprise performing a bias correction technique by adjusting the elements of the data set based on a centroid of the data set. The transformation is performed according to a transformation function, which may define the transformation based on the training class set. In certain embodiments of the methods described above, the the bias correction technique comprises subtracting a component of the centroid from each element of the data set. For example, the result of the bias correction technique may be that each element of the training data set, the test data set, or both the training and test data sets is "recentered" by taking into account the centroids of each class represented in the data set. In certain embodiments of the methods described above, the step of transforming the training data set, transforming the test data set, or both steps of transforming the training data set and transforming the test data set comprise applying a rotation, a shear, a shift, a linear transformation, or a non-linear transformation.

In certain embodiments of the methods described above, the methods further comprise comparing the first test class set to the second test class set for each of the plurality of iterations. As a result of the comparison, the first test class set and the second test class set may be said to differ if any single element of the first test class set differs from a corresponding element of the second test class set. In general, a threshold may be set such that the first test class set and the second test class set are said to differ if at least a predetermined number of elements in the first test class set differs from the corresponding elements in the second test class set.

In certain embodiments of the methods described above, the methods further comprise generating the second classifier for the transformed training data set by applying a machine learning technique to the transformed training data set and the training class set for each of the plurality of iterations. In certain embodiments of the methods described above, the transforming of the test data set involves the same transformation as the transformation of the transforming of the training data set. In certain embodiments of the methods described above, the methods further comprise providing the second test class set to a display device, a printing device, or a storing device. In certain embodiments of the methods described above, the methods further comprise computing a performance metric of the second classifier based on an error rate. In certain embodiments, linear classifiers such as but not limited to Linear Discriminant Analysis (LDA), logistic regression, support vector machine, naive Bayes classifier, are preferred.

The computer systems of the present invention comprise means for implementing the various embodiments of the methods, as described above. For example, a computer program product is described, the product comprising computer-readable instructions that, when executed in a computerized system comprising at least one processor, cause the processor to carry out one or more steps of any of the methods described above. In another example, a computerized system is described, the system comprising a processor configured with non-transitory computer-readable instructions that, when executed, cause the processor to carry out any of the methods described above. The computer program product and the computerized methods described herein may be implemented in a computerized system having one or more computing devices, each including one or more processors. Generally, the computerized systems described herein may comprise one or more engines, which include a processor or devices, such as a computer, microprocessor, logic device or other device or processor that is configured with hardware, firmware, and software to carry out one or more of the computerized methods described herein. Any one or more of these engines may be physically separable from any one or more other engines, or may include multiple physically separable components, such as separate processors on common or different circuit boards. The computer systems of the present invention comprises means for implementing the methods and its various embodiments as described above. The engines may be interconnected from time to time, and further connected from time to time to one or more databases, including a perturbations database, a measurables database, an experimental data database and a literature database. The computerized system described herein may include a distributed computerized system having one or more processors and engines that communicate through a network interface. Such an implementation may be appropriate for distributed computing over multiple communication systems.

BRIEF DESCRIPTION OF THE DRAWINGS

Further features of the disclosure, its nature and various advantages, will be apparent upon consideration of the following detailed description, taken in conjunction with the accompanying drawings, in which like reference characters refer to like parts throughout, and in which.

DETAILED DESCRIPTION

To provide an overall understanding of the systems and methods described herein, certain illustrative embodiments will now be described, including systems and methods for identifying gene biomarker signatures. However, it will be understood by one of ordinary skill in the art that the systems, computer program products and methods described herein may be adapted and modified for other suitable applications, such as any data classification application, and that such other additions and modifications will not depart from the scope thereof. Generally, the computerized systems described herein may comprise one or more engines, processor or devices, such as a computer, microprocessor, or logic device that is configured with hardware, firmware, and software to carry out one or more of the computerized methods described herein.

Figure 1:
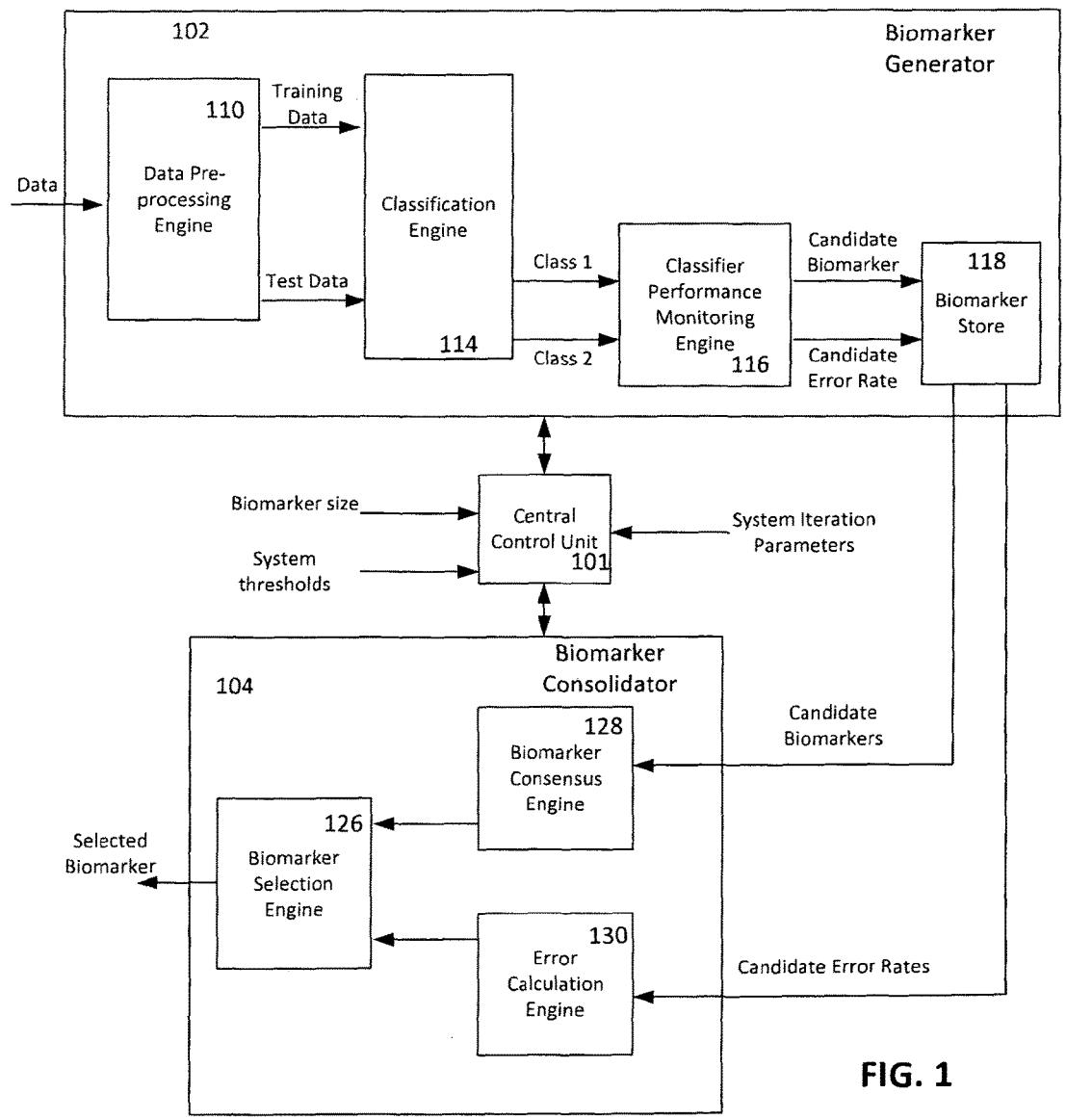
FIG. 1 depicts an exemplary system for identifying one or more biomarker signatures.

FIG. 1 depicts an exemplary system 100 for identifying one or more biomarker signatures in which the classification techniques disclosed herein may be implemented. The system 100 includes a biomarker generator 102 and a biomarker consolidator 104. The system 100 further includes a central control unit (CCU) 101 for controlling certain aspects of the operation of the biomarker generator 102 and the biomarker consolidator 104. During operation, data such as gene expression data is received at the biomarker generator 102. The biomarker generator 102 processes the data to generate a plurality of candidate biomarkers and corresponding error rates. The biomarker consolidator 104 receives these candidate biomarkers and error rates and selects a suitable biomarker having an optimal performance measure and size.

The biomarker generator 102 includes several components for processing data and generating a set of candidate biomarkers and candidate error rates. In particular, the biomarker generator includes a data pre-processing engine 110 for splitting the data into a training data set and a test data set. The biomarker generator 102 includes a classification engine 114 for receiving the training data set and the test data set and classifying the elements of the test data set into one of two or more classes (e.g., diseased and non-diseased, susceptible and immune and diseased, etc.). The biomarker generator 102 includes a classifier performance monitoring engine 116 for determining the performance of the classifier as applied to the test data selected by the data pre-processing engine 110. The classifier performance monitoring engine 116 identifies candidate biomarkers based on the classifier (e.g., the components of the elements of the data set that are most important to the classification) and generates performance measures, which may include candidate error rates, for one or more candidate biomarkers. The biomarker generator 102 further includes a biomarker store 118 for storing one or more candidate biomarkers and candidate performance measures.

The biomarker generator may be controlled by the CCU 101, which in turn may be automatically controlled or user-operated. In certain embodiments, the biomarker generator 102 may operate to generate a plurality of candidate biomarkers, each time splitting the data randomly into training and test data sets. To generate such a plurality of candidate biomarkers, the operation of the biomarker generator 102 may be iterated a plurality of times. CCU 101 may receive one or more system iteration parameters including a desired number of candidate biomarkers, which in turn may be used to determine the number of times the operation of the biomarker generator 102 may be iterated. The CCU 101 may also receive other system parameters including a desired biomarker size which may be representative of the number of components in a biomarker (e.g., the number of genes in a biomarker gene signature). The biomarker size information may be used by the classifier performance monitoring engine 116 for generating candidate biomarkers from the training data. The operation of the biomarker generator 102, and the classification engine 114 in particular, are described in more detail with reference to FIGS. 2-4.

The biomarker generator 102 generates one or more candidate biomarkers and candidate error rates, which is used by the biomarker consolidator 104 for generating robust biomarkers. The biomarker consolidator 104 includes a biomarker consensus engine 128 which receives a plurality of candidate biomarkers and generates a new biomarker signature having the most frequently occurring genes across the plurality of candidate biomarkers. The biomarker consolidator 104 includes an error calculation engine 130 for determining an overall error rate across the plurality of candidate biomarkers. Similar to the biomarker generator 102, the biomarker consolidator 104 may also be controlled by the CCU 101, which in turn may be automatically controlled or user-operated. The CCU 101 may receive and/or determine suitable threshold values for the minimum biomarker size, and use this information to determine the number of iterations to operate both the biomarker generator 102 and the biomarker consolidator 104. In one embodiment, during each iteration, the CCU 101 decreases the biomarker size by one and iterates both the biomarker generator 102 and the biomarker consolidator 104 until the threshold is reached. In such an embodiment, the biomarker consensus engine 128 outputs a new biomarker signature and a new overall error rate for each iteration. The biomarker consensus engine 128 thus outputs set of new biomarker signatures each having a different size varying from the threshold value up to a maximum biomarker size. The biomarker consolidator 104 further includes a biomarker selection engine 126 which reviews the performance measure or error rate of each of these new biomarker signatures and selects the optimal biomarker for output. The operation of the biomarker consolidator 104 and its respective engines are described in more detail with reference to FIGS. 2-4.

Figure 3A:
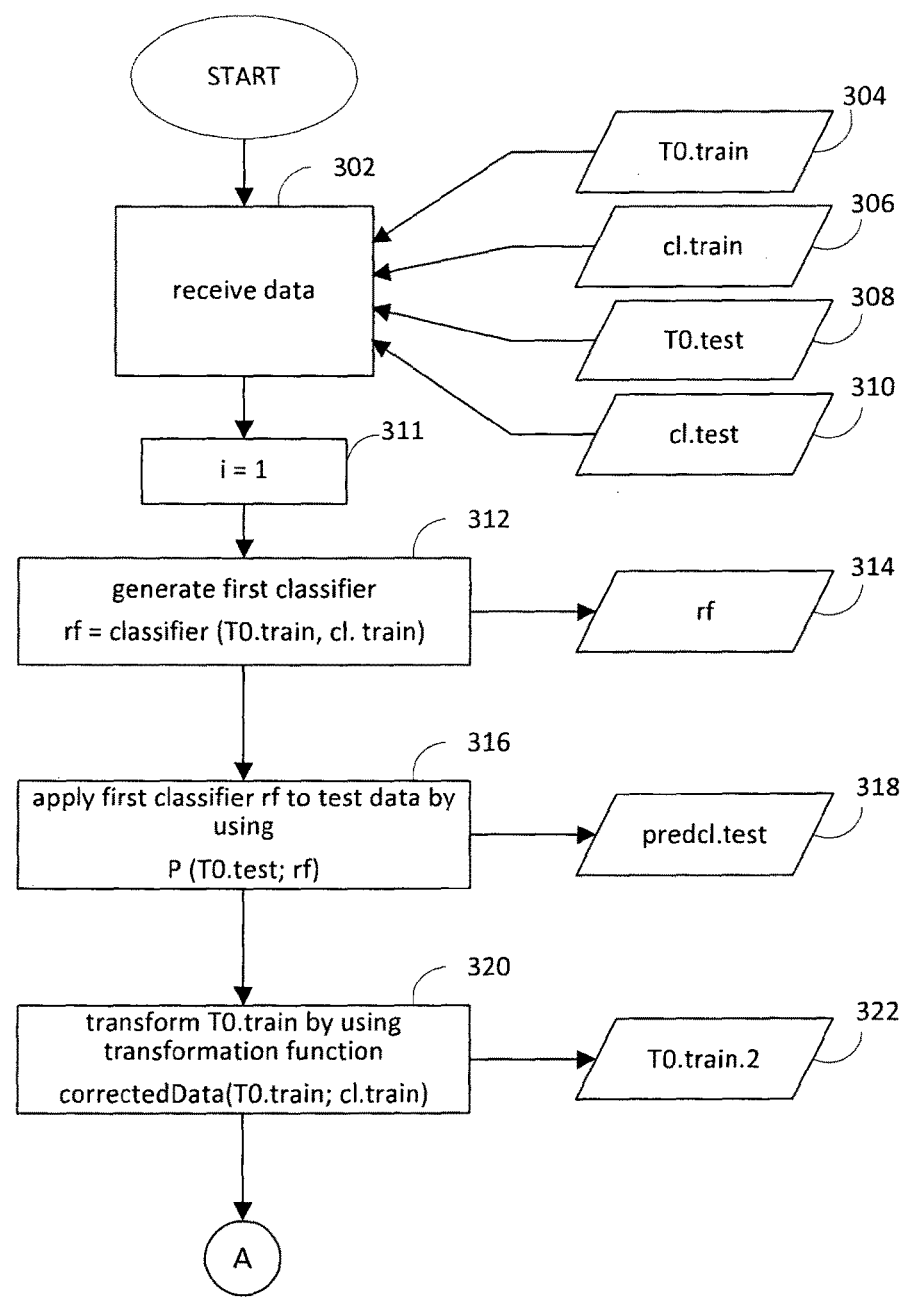
FIGS. 3A and 3B are flow diagrams of an exemplary process for classifying a data set.
Figure 3B:
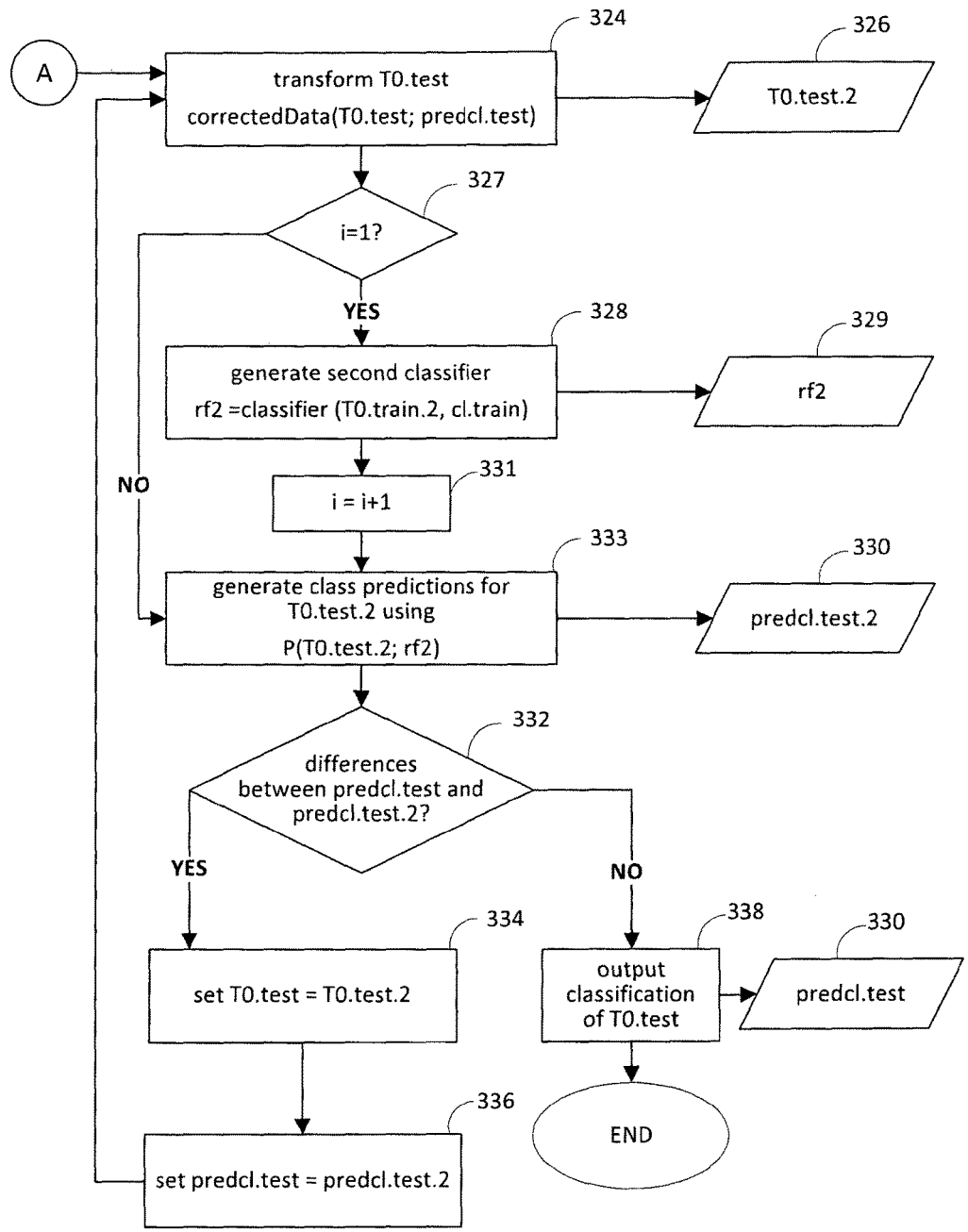

FIGS. 3A and 3B are flow diagrams of an exemplary process for classifying a data set. At step 302, the classification engine 114 receives training data and test data. As described below, the classification engine 114 uses the training data to develop one or more classifiers, then applies the one or more classifiers to the test data. As illustrated in FIGS. 3A and 3B, the training data includes a training data set T0.train 304 and a training class set c1.train 306. Each element in the training data set T0.train 304 represents a data sample (e.g., a vector of expression data from a particular patient) and corresponds to a known class identifier in the training class set c1.train 306. For example, in a three-class scenario, the first element in the training data set T0.train 304 may represent gene expression data for a patient with a particular disease, and may correspond to a first element "Disease Positive" in the training class set c1.train 306; the second element in the training data set T0.train 304 may represent gene expression data for a patient who is resistant to or immune to the particular disease, and may correspond to a second element "Disease Immune" in the training class set c1.train 306; and the third element in the training data set T0.train 304 may represent gene expression data for a patient without the particular disease, and may correspond to a third element "Disease Free" in the training class set c1.train 306. The test data received at step 302 includes the test data set T0.test 308, which represents the same underlying type of data as the data samples in the training data set T0.train 304, but may represent samples taken from different patients or different experiments, for example. Optionally, the classification engine 114 also receives a test class set c1.test 310 that includes the known class identifiers for the data samples in the test data set, which may be used to evaluate the performance of the classifier generated by the classification engine 114 when that classifier is applied to the test data set T0.test 308. In some implementations, no known classes for the data samples in the test data set T0.test 308 are available, and thus the test class set c1.test 310 is not provided to the classification engine 114.

Generally, the data received at step 302 may represent any experimental or otherwise obtained data from which a classification may be drawn, such as expression values of a plurality of different genes in a sample, and/or a variety of a phenotypic characteristics such as levels of any biologically significant analyte. In certain embodiments, the data sets may include expression level data for a disease condition and for a control condition. As used herein, the term "gene expression level" may refer to the amount of a molecule encoded by the gene, e.g., an RNA or polypeptide. The expression level of an mRNA molecule may include the amount of mRNA (which is determined by the transcriptional activity of the gene encoding the mRNA) and the stability of the mRNA (which is determined by the half-life of the mRNA). The gene expression level may also include the amount of a polypeptide corresponding to a given amino acid sequence encoded by a gene. Accordingly, the expression level of a gene can correspond to the amount of mRNA transcribed from the gene, the amount of polypeptide encoded by the gene, or both. Expression levels of a gene may be further categorized by expression levels of different forms of gene products. For example, RNA molecules encoded by a gene may include differentially expressed splice variants, transcripts having different start or stop sites, and/or other differentially processed forms. Polypeptides encoded by a gene may encompass cleaved and/or modified forms of polypeptides. Polypeptides can be modified by phosphorylation, lipidation, prenylation, sulfation, hydroxylation, acetylation, ribosylation, farnesylation, addition of carbohydrates, and the like. Further, multiple forms of a polypeptide having a given type of modification can exist. For example, a polypeptide may be phosphorylated at multiple sites and express different levels of differentially phosphorylated proteins.

In certain embodiments the gene expression level in a cell or tissue may be represented by a gene expression profile. Gene expression profiles may refers to a characteristic representation of a gene's expression level in a specimen such as a cell or tissue. The determination of a gene expression profile in a specimen from an individual is representative of the gene expression state of the individual. A gene expression profile reflects the expression of messenger RNA or polypeptide or a form thereof encoded by one or more genes in a cell or tissue. An expression profile may generally refer to a profile of biomolecules (nucleic acids, proteins, carbohydrates) which shows different expression patterns among different cells or tissue. A data sample representing a gene expression profile may be stored as a vector of expression levels, with each entry in the vector corresponding to a particular biomolecule or other biological entity.

In certain embodiments, the data sets may include elements representing gene expression values of a plurality of different genes in a sample. In other embodiments, the data set may include elements that represent peaks detected by mass spectrometry. Generally, each data set may include data samples that each correspond to one of a plurality of biological state classes. For example, a biological state class can include, but is not limited to: presence/absence of a disease in the source of the sample (i.e., a patient from whom the sample is obtained); stage of a disease; risk for a disease; likelihood of recurrence of disease; a shared genotype at one or more genetic loci (e.g., a common HLA haplotype; a mutation in a gene; modification of a gene, such as methylation, etc.); exposure to an agent (e.g., such as a toxic substance or a potentially toxic substance, an environmental pollutant, a candidate drug, etc.) or condition (temperature, pH, etc); a demographic characteristic (age, gender, weight; family history; history of preexisting conditions, etc.); resistance to agent, sensitivity to an agent (e.g., responsiveness to a drug) and the like.

Data sets may be independent of each other to reduce collection bias in ultimate classifier selection. For example, they can be collected from multiple sources and may be collected at different times and from different locations using different exclusion or inclusion criteria, i.e., the data sets may be relatively heterogeneous when considering characteristics outside of the characteristic defining the biological state class. Factors contributing to heterogeneity include, but are not limited to, biological variability due to sex, age, ethnicity; individual variability due to eating, exercise, sleeping behavior; and sample handling variability due to clinical protocols for blood processing. However, a biological state class may comprise one or more common characteristics (e.g., the sample sources may represent individuals having a disease and the same gender or one or more other common demographic characteristics). In certain embodiments, the data sets from multiple sources are generated by collection of samples from the same population of patients at different times and/or under different conditions.

In certain embodiments, a plurality of data sets is obtained from a plurality of different clinical trial sites and each data set comprises a plurality of patient samples obtained at each individual trial site. Sample types include, but are not limited to, blood, serum, plasma, nipple aspirate, urine, tears, saliva, spinal fluid, lymph, cell and/or tissue lysates, laser microdissected tissue or cell samples, embedded cells or tissues (e.g., in paraffin blocks or frozen); fresh or archival samples (e.g., from autopsies). A sample can be derived, for example, from cell or tissue cultures in vitro. Alternatively, a sample can be derived from a living organism or from a population of organisms, such as single-celled organisms. In one example, when identifying biomarkers for a particular cancer, blood samples for might be collected from subjects selected by independent groups at two different test sites, thereby providing the samples from which the independent data sets will be developed.

In some implementations, the training and test sets are generated by the data pre-processing engine 110 (FIG. 1), which receives bulk data and splits the bulk data into a training data set and a test data set. In certain embodiments, the data pre-processing engine 110 randomly splits the data into these two groups. Randomly splitting the data may be desirable for predicting classes and generating robust gene signature. In other embodiments, the data pre-processing engine 110 splits the data into two or more groups based on the type or label of the data. Generally, the data can be split into a training data set and a test data set in any suitable way as desired without departing from the scope of the present disclosure. The training data set and the test data set may have any suitable size and may be of the same or different sizes. In certain embodiments, the data pre-processing engine 110 may discard one or more pieces of data prior to splitting the data into the training and test data sets. In certain embodiments, the data pre-processing engine 110 may discard one or more pieces of data from the training data set and/or the test data set prior to any further processing.

Figure 2:
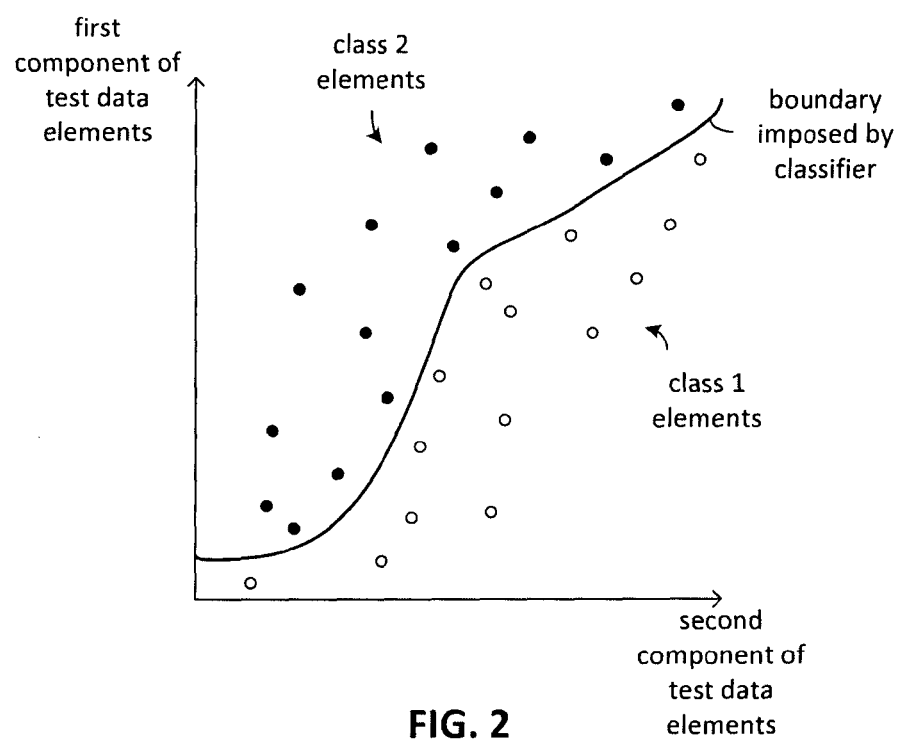
FIG. 2 illustrates the classification of elements in a data set.

At step 311, the classification engine 114 sets a counter variable i equal to 1. At step 312, the classification engine 114 generates a first classifier rf 314 based on the training data set T0.train 304 and the training class set c1.train 306. FIG. 2 illustrates the classification of elements in a data set. The classification engine 114 may use any one or more known machine-learning algorithms at step 312, including but not limited to support vector machine techniques, linear discriminant analysis techniques, Random Forest techniques, k-nearest neighbors techniques, partial least squares techniques (including techniques that combine partial least squares and linear discriminant analysis features), logistic regression techniques, neural network-based techniques, decision tree-based techniques and shrunken centroid techniques (e.g., as described by Tibshirani, Hastle, Narasimhan and Chu in "Diagnosis of multiple cancer types by shrunken centroids of gene expression," PNAS, v. 99, n. 10, 2002). A number of such techniques are available as packages for the R programming language, including lda, svm, randomForest, knn, pls.lda and pamr, corresponding to linear discriminant analysis, support vector machine, random forest (Breiman, *Machine Learning*, 45(1):5-32 (2001)), k-nearest neighbors (Bishop, Neural Networks for Pattern Recognition, ed. O.U. Press, 1995), partial least squares discriminant analysis, and PAMR (Tibshirani et al., *Proc Natl Acad Sci USA*, 99(10):6567-6572 (2002)). The classification engine 114 may store the first classifier rf 314 in a memory at step 312.

At step 316, the classification engine 114 generates a set of predicted test classifications predc1.test 318 by applying the first classifier rf 314 (generated at step 312) to the test data set T0.test 308. The classification engine 114 may store the predicted classifications predc1.test 318 in a memory at step 316.

At step 320, the classification engine 114 transforms the training data set T0.train 304. This transformation proceeds according to a transformation function, correctedData, which transforms the training data set T0.train 304 based on the training class set c1.train 306. The result of the transformation of step 310 is a transformed training data set, T0.train.2 322, which the classification engine 114 may store in a memory. In some implementations, the transformation performed by the classification engine 114 at step 320 includes a bias correction technique. For example, the transformation may "recenter" the training data set T0.train 304 by adjusting the elements of the training data set T0.train 304 with respect to the centroid of the data set taken as a whole, or the centroids of each class represented in the data set.

One particular recentering technique involves centering the elements of the training data set T0.train 304 based on the center of centroids of different groups. If there are n data samples in the training data set T0.train 304, and each data sample is a vector with p entries (e.g., representing expression levels for p different genes), let xij represent the ith entry of data sample j. If the training class set c1.train 308 represents K different classes, let Ck represent the indices of the nk samples in class k. The classification engine 114 may calculate the ith component of the centroid of class k as $$\bar{x}_{ik} = \sum_{j \in C_k} \frac{x_{ij}}{n_k}. \tag{1}$$

and may compute the ith component of the center of the class centroids as $$\bar{x}_i^c = \sum_{k=1}^{K} \frac{\bar{x}_{ik}}{K}. \tag{2}$$

The classification engine 114 may also calculate the ith component of the overall centroid as:

$$\bar{x}_i = \sum_{j=1}^{n} \frac{x_{ij}}{n}. \tag{3}$$

The classification engine 114 may then perform a transformation that includes adjusting the ith entry in each element of the training data set T0.train 304 by adding the difference given by:

$$\Delta = -\bar{x}_i^c. \tag{4}$$

In some implementations, the transformation performed at step 320 includes a shift other than the one described above with reference to Eqs. 1-4, a rotation, a shear, a combination of these transformations, or any other linear or non-linear transformation.

At step 324, the classification engine 114 transforms the test data set T0.test 308. The transformation applied to the test data set T0.test 308, correctedData, is the same type of transformation applied to the training data set T0.train 304 at step 320, but applied with respect to the arguments T0.test 308 and predc1.test 318 instead of T0.train 304 and predc1.train 314. For example, if the elements of the training data set T0.train 304 are adjusted at step 320 by the value of Δ given by Eq. 4 as calculated with respect to the centroids of the classes of the training data set T0.train 304, then the elements of the test data set T0.test 308 are adjusted at step 324 by the value of Δ given by Eq. 4 as calculated with respect to the centroids of the classes of the test data set T0.test 308. The result of the transformation of step 324 is a transformed test data set, T0.test.2 326, which the classification engine 114 may store in a memory.

At step 327, the classification engine 114 determines whether the value of the iteration counter i is equal to 1. If so, the classification engine 114 proceeds to execute step 328, in which the classification engine 114 uses the transformed training data set T0.train.2 322 and the training class set c1.train 306 to generate a second classifier rf2 329. As described above with reference to Step 332, and to step 336, any machine-learning technique may be applied to generate the classifier at step 328. The second classifier rf2 329 may be of the same type as the first classifier rf 314 (e.g., both SVM classifiers), or of a different type.

At step 331, the classification engine 114 increments the iteration counter i, then proceeds to execute step 333, in which the classification engine 114 applies the second classifier rf2 329 to the transformed test data set T0.test.2 326 (as generated by the classification engine 114 at step 324). The output of step 333 is a set of predicted classifications predc1.test.2 330 for the transformed data set T0.test.2 326. The classification engine 114 may output the predicted classifications to a display device, a printing device, a storing device, another device in communication with the classification engine 114 across a network or any other device internal or external to the system 100.

At step 332, the classification engine 114 determines whether there are any differences between the classifications of the predicted classification set predc1.test 318 (as generated at step 316) and the predicted classifications set predc1.test.2 330 (as generated at step 328). If the sets of predicted classifications agree (i.e., for each data sample in the test data set T0.test 308, the predicted class for that data sample is the same between the two predicted classifications set), then the classification engine 114 proceeds to step 338 and outputs the predicted classification set predc1.test.2 330 (equivalently, the predicted classification set predc1.test 318) as the final classification of the test data set T0.test 308.

If the classification engine 114 identifies differences between the classification data set predc1.test 318 and the classification data set predc1.test.2 330, the classification engine 114 proceeds to step 334 and replaces the previously stored value of the test data set T0.test 308 with the value of the transformed test data set T0.test.2 326 (as generated by the transformation of step 324). As a result, the test data set T0.test 308 has the values of the transformed test data set T0.test.2 326. The classification engine 114 proceeds to step 336 and replaces the previously stored value of the predicted classification set predc1.test 318 (as generated at step 316) with the value of the predicted classification set predc1.test.2 330 (as generated at step 328). As a result, the predicted classification set predc1.test 318 has the values of the predicted classification set predc1.test.2 330.

Once the value of the test data set T0.test 308 has been updated with the value of the transformed test data set T0.test.2 326 and the predicted classification set predc1.test 318 has been updated with the values of the predicted classification set predc1.test.2 330, the classification engine 114 returns to step 324 to perform a new transformation and iterates this process until the classification engine 114 determines that there is no difference between the predicted classifications (at step 332).

The classifier performance monitoring engine 116 may analyze the performance of the final classification produced by the classification engine 114 at the conclusion of the process of FIG. 3 using a suitable performance metric. In certain embodiments, the performance metric may include an error rate. The performance metric may also include the number of correct predictions divided by the total predictions attempted. The performance metric may be any suitable measure without departing from the scope of the present disclosure.

Implementations of the present subject matter can include, but are not limited to, systems methods and computer program products comprising one or more features as described herein as well as articles that comprise a machine-readable medium operable to cause one or more machines (e.g., computers, robots) to result in operations described herein. The methods described herein can be implemented by one or more processors or engines residing in a single computing system or multiple computing systems. Such multiple computing systems can be connected and can exchange data and/or commands or other instructions or the like via one or more connections, including but not limited to a connection over a network (e.g. the Internet, a wireless wide area network, a local area network, a wide area network, a wired network, or the like), via a direct connection between one or more of the multiple computing systems.

Figure 4:
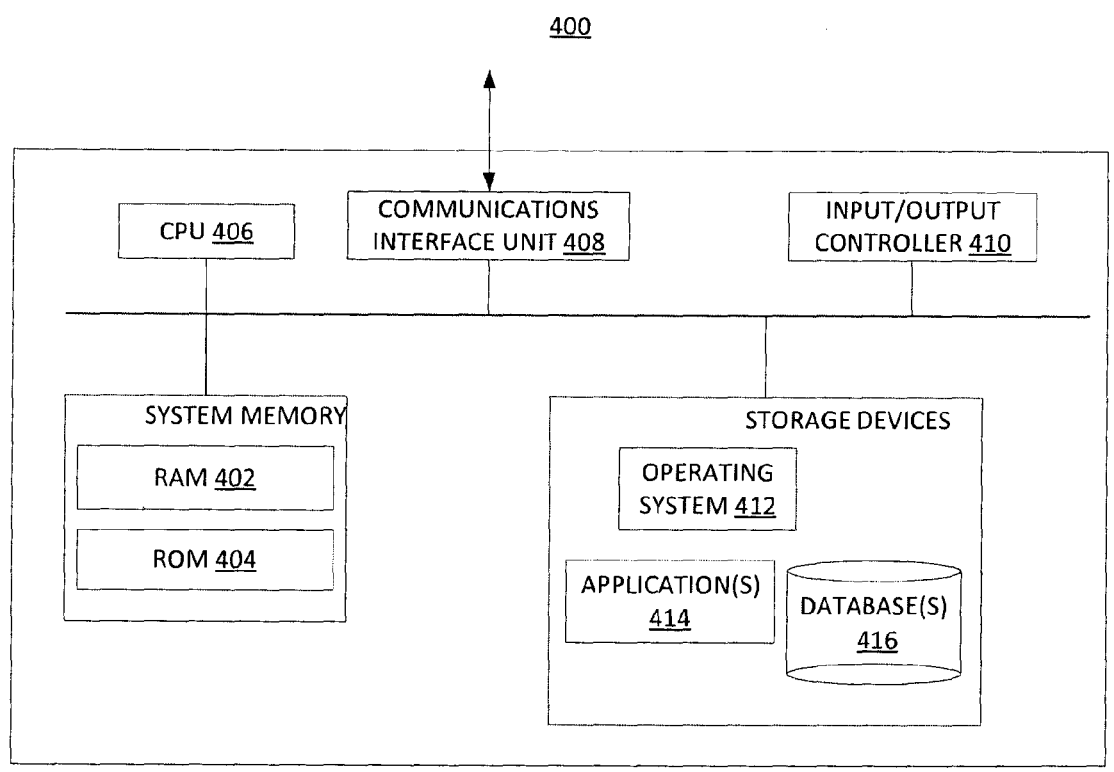
FIG. 4 is a block diagram of a computing device, such as any of the components of the system of FIG. 1.

FIG. 4 is a block diagram of a computing device, such as any of the components of system 100 of FIG. 1 including circuitry for performing processes described with reference to FIGS. 1-3. Each of the components of system 100 may be implemented on one or more computing devices 400. In certain aspects, a plurality of the above-components and databases may be included within one computing device 400. In certain implementations, a component and a database may be implemented across several computing devices 400.

The computing device 400 comprises at least one communications interface unit, an input/output controller 410, system memory, and one or more data storage devices. The system memory includes at least one random access memory (RAM 402) and at least one read-only memory (ROM 404). All of these elements are in communication with a central processing unit (CPU 406) to facilitate the operation of the computing device 400. The computing device 400 may be configured in many different ways. For example, the computing device 400 may be a conventional standalone computer or alternatively, the functions of computing device 400 may be distributed across multiple computer systems and architectures. The computing device 400 may be configured to perform some or all of data-splitting, differentiating, classifying, scoring, ranking and storing operations. In FIG. 4, the computing device 400 is linked, via network or local network, to other servers or systems.

The computing device 400 may be configured in a distributed architecture, wherein databases and processors are housed in separate units or locations. Some such units perform primary processing functions and contain at a minimum a general controller or a processor and a system memory. In such an aspect, each of these units is attached via the communications interface unit 408 to a communications hub or port (not shown) that serves as a primary communication link with other servers, client or user computers and other related devices. The communications hub or port may have minimal processing capability itself, serving primarily as a communications router. A variety of communications protocols may be part of the system, including, but not limited to: Ethernet, SAP, SAS™, ATP, BLUETOOTH™, GSM and TCP/IP.

The CPU 406 comprises a processor, such as one or more conventional microprocessors and one or more supplementary co-processors such as math co-processors for offloading workload from the CPU 406. The CPU 406 is in communication with the communications interface unit 408 and the input/output controller 410, through which the CPU 406 communicates with other devices such as other servers, user terminals, or devices. The communications interface unit 408 and the input/output controller 410 may include multiple communication channels for simultaneous communication with, for example, other processors, servers or client terminals. Devices in communication with each other need not be continually transmitting to each other. On the contrary, such devices need only transmit to each other as necessary, may actually refrain from exchanging data most of the time, and may require several steps to be performed to establish a communication link between the devices.

The CPU 406 is also in communication with the data storage device. The data storage device may comprise an appropriate combination of magnetic, optical or semiconductor memory, and may include, for example, RAM 402, ROM 404, flash drive, an optical disc such as a compact disc or a hard disk or drive. The CPU 406 and the data storage device each may be, for example, located entirely within a single computer or other computing device; or connected to each other by a communication medium, such as a USB port, serial port cable, a coaxial cable, an Ethernet type cable, a telephone line, a radio frequency transceiver or other similar wireless or wired medium or combination of the foregoing. For example, the CPU 406 may be connected to the data storage device via the communications interface unit 408.

The CPU 406 may be configured to perform one or more particular processing functions.

The data storage device may store, for example, (i) an operating system 412 for the computing device 400; (ii) one or more applications 414 (e.g., computer program code or a computer program product) adapted to direct the CPU 406 in accordance with the systems and methods described here, and particularly in accordance with the processes described in detail with regard to the CPU 406; or (iii) database(s) 416 adapted to store information that may be utilized to store information required by the program. In some aspects, the database(s) includes a database storing experimental data, and published literature models.

The operating system 412 and applications 414 may be stored, for example, in a compressed, an uncompiled and an encrypted format, and may include computer program code. The instructions of the program may be read into a main memory of the processor from a computer-readable medium other than the data storage device, such as from the ROM 404 or from the RAM 402. While execution of sequences of instructions in the program causes the CPU 406 to perform the process steps described herein, hard-wired circuitry may be used in place of, or in combination with, software instructions for implementation of the processes of the present invention. Thus, the systems and methods described are not limited to any specific combination of hardware and software.

Suitable computer program code may be provided for performing one or more functions in relation to modeling, scoring and aggregating as described herein. The program also may include program elements such as an operating system 412, a database management system and "device drivers" that allow the processor to interface with computer peripheral devices (e.g., a video display, a keyboard, a computer mouse, etc.) via the input/output controller 410.

A computer program product comprising computer-readable instructions is also provided. The computer-readable instructions, when loaded and executed on a computer system, cause the computer system to operate according to the method, or one or more steps of the method described above. The term "computer-readable medium" as used herein refers to any non-transitory medium that provides or participates in providing instructions to the processor of the computing device 400 (or any other processor of a device described herein) for execution. Such a medium may take many forms, including but not limited to, non-volatile media and volatile media. Non-volatile media include, for example, optical, magnetic, or opto-magnetic disks, or integrated circuit memory, such as flash memory. Volatile media include dynamic random access memory (DRAM), which typically constitutes the main memory. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM or EEPROM (electronically erasable programmable read-only memory), a FLASH-EEPROM, any other memory chip or cartridge, or any other non-transitory medium from which a computer can read.

Various forms of computer readable media may be involved in carrying one or more sequences of one or more instructions to the CPU 406 (or any other processor of a device described herein) for execution. For example, the instructions may initially be borne on a magnetic disk of a remote computer (not shown). The remote computer can load the instructions into its dynamic memory and send the instructions over an Ethernet connection, cable line, or even telephone line using a modem. A communications device local to a computing device 400 (e.g., a server) can receive the data on the respective communications line and place the data on a system bus for the processor. The system bus carries the data to main memory, from which the processor retrieves and executes the instructions. The instructions received by main memory may optionally be stored in memory either before or after execution by the processor. In addition, instructions may be received via a communication port as electrical, electromagnetic or optical signals, which are exemplary forms of wireless communications or data streams that carry various types of information.

EXAMPLE

The following public datasets are downloaded from the Gene Expression Omnibus (GEO) (http://www.ncbi.nlm.nih.gov/geo/) repository:

a. GSE10106 (www.ncbi.nlm.nih.gov/geo/query/acc.cgi?acc=GSE10106)
b. GSE10135 (www.ncbi.nlm.nih.gov/geo/query/acc.cgi?acc=GSE10135)
c. GSE11906 (www.ncbi.nlm.nih.gov/geo/query/acc.cgi?acc=GSE11906)
d. GSE11952 (www.ncbi.nlm.nih.gov/geo/query/acc.cgi?acc=GSE11952)
e. GSE13933 (www.ncbi.nlm.nih.gov/geo/query/acc.cgi?acc=GSE13933)
f. GSE19407 (www.ncbi.nlm.nih.gov/geo/query/acc.cgi?acc=GSE19407)
g. GSE19667 (www.ncbi.nlm.nih.gov/geo/query/acc.cgi?acc=GSE19667)
h. GSE20257 (www.ncbi.nlm.nih.gov/geo/query/acc.cgi?acc=GSE20257)
i. GSE5058 (www.ncbi.nlm.nih.gov/geo/query/acc.cgi?acc=GSE5058)
j. GSE7832 (www.ncbi.nlm.nih.gov/geo/query/acc.cgi?acc=GSE7832)
k. GSE8545 (www.ncbi.nlm.nih.gov/geo/query/acc.cgi?acc=GSE8545).

Figure 5:
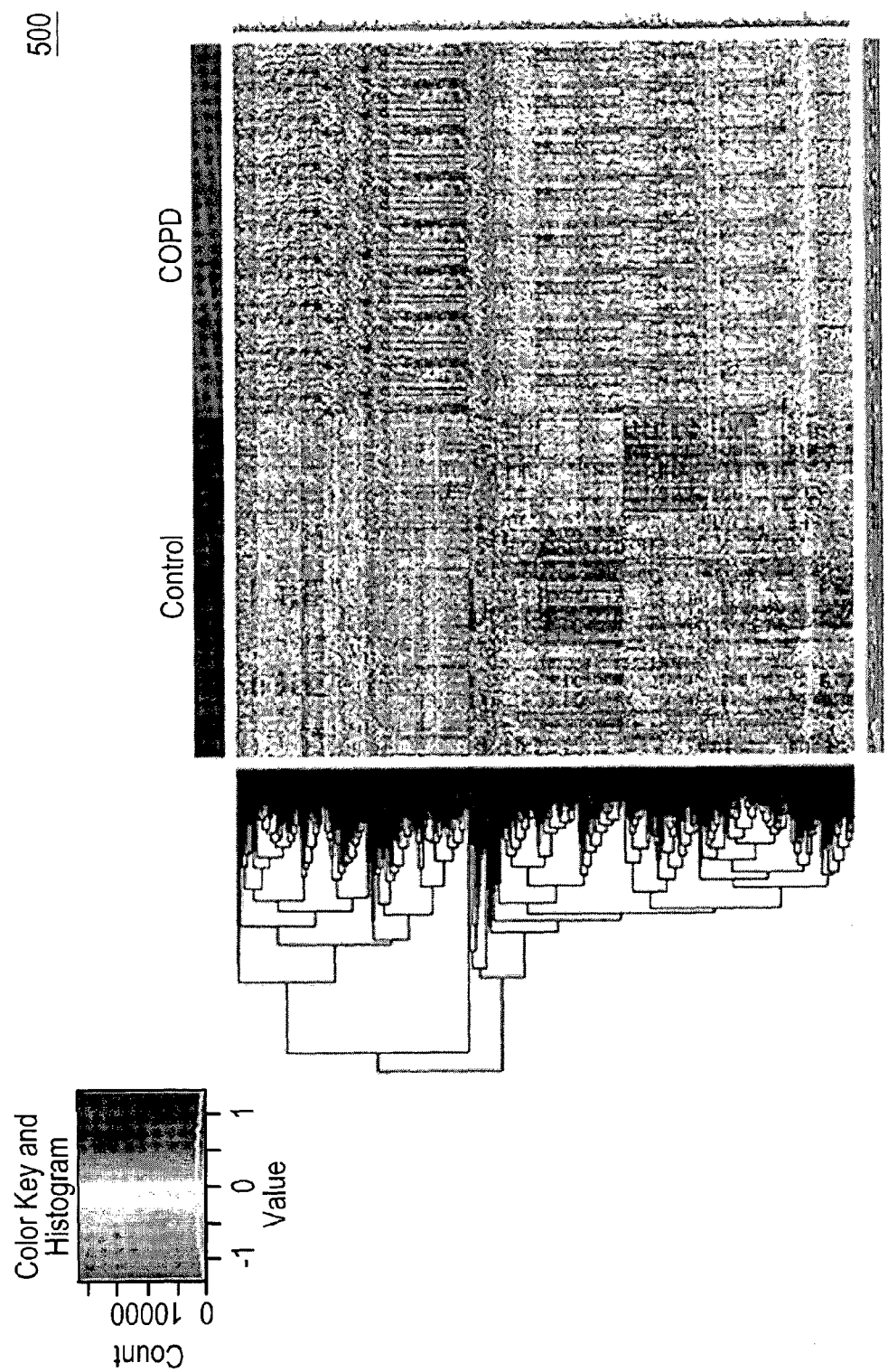
FIG. 5 is a heatmap of a gene signature in a training data set.

The training datasets are on the Affymetrix platform (HGU-133+2). Raw data files are read by the ReadAffy function of the affy package (Gautier, 2004) belonging to Bioconductor (Gentleman, 2004) in R (R Development Core Team, 2007), and the quality is controlled by: generating RNA degradation plots (with the AffyRNAdeg function of the affy package), NUSE and RLE plots (with the function affyPLM (Brettschneider, 2008)), and calculating the MA(RLE) values; excluding arrays from the training datasets that fell below a set of thresholds on the quality control checks or that are duplicated in the above datasets; and normalizing arrays that pass quality control checks using the gcrma algorithm (Wu, 2004). Training set sample classifications are obtained from the series matrix file of the GEO database for each dataset. The output consists of a gene expression matrix with 54675 probesets for 233 samples (28 COPD samples and 205 control sample). To make a balanced data set, the COPD samples were multiple time to obtain 224 COPD samples before the Duel Ensemble method as described in copending U.S. provisional application 61/662,812 is applied. With a combined data set which contains 205 control and 224 COPD patients, a gene signature with 409 genes was built. 850 binary values were used in the random vectors. The classification methods used in the method included the following R packages: lda, svm, randomForest, knn, pls.lda and pamr. Maximum iteration was set to be 5000. The Matthew's Correlation Coefficient (MCC) and accuracy in cross validation process in training data set is 0.743 and 0.87 respectively. The heatmap of the gene signature in training data set is shown in FIG. 5. In the heatmap of FIG. 5, the gene expression value was centered by row. The colors of the heatmap may not be clearly shown in grey scale, but the data of FIG. 5 show that control data are shown on the left, and COPD data are shown on the right. The test data set is an unpublished data set obtained from a commercial supplier (Genelogic), which contains 16 control samples and 24 COPD samples. Without applying the transformation invariant method of the invention, the gene signature generated by Dual Ensemble correctly predicted 29 samples out of total 40 samples. The accuracy is 0.725, and the MCC is 0.527. In the 16 control samples, the gene signature correctly predicted 15 as control but erroneously predicted 1 as COPD. Among the 24 COPD samples, the gene signature correctly predicted 14 as COPD samples but erroneously predicted 10 as control.

However, when the transformation invariant method was applied with a shift according to the center of two or multiple classes and a maximum iterations set to 100. The same gene signature correctly predicted 30 samples out of total 40 samples. The accuracy is 0.75, and the MCC is 0.533. In the 16 control samples, the gene signature correctly predicted 14 as control but erroneously predicted 2 as COPD. Among the 24 COPD samples, the gene signature correctly predicted 16 as COPD samples but erroneously predicted 8 as control.

While implementations of the invention have been particularly shown and described with reference to specific examples, it should be understood by those skilled in the art that various changes in form and detail may be made therein without departing from the spirit and scope of the disclosure.

The invention claimed is:

1. A computer-implemented method of classifying a data set into two or more classes, comprising:
   (a) receiving, by a biomarker generator, a training data set and a training class set, the training class set including a set of known labels, each known label identifying a class associated with each element in the training data set;
   (b) receiving, by the biomarker generator, a test data set;
   (c) generating, by the biomarker generator, a first classifier for the training data set by applying a first machine learning technique to the training data set and the training class set;
   (d) generating, by the biomarker generator, a first test class set by classifying the elements in the test data set according to the first classifier;
   (e) transforming, by the biomarker generator, the training data set by shifting the elements in the training data set by an amount corresponding to a center of a set of training class centroids, wherein each training class centroid is representative of a center of a subset of elements in the training data set;
   (f) for each of a plurality of iterations:
      (i) transforming, by the biomarker generator, the test data set by shifting the elements in the test data set by an amount corresponding to a center of a set of test class centroids, wherein each test class centroid is representative of a center of a subset of elements in the test data set;
      (ii) generating, by the biomarker generator, a second test class set by classifying the elements in the transformed test data set according to a second classifier, wherein the second classifier is generated by applying a second machine learning technique to the transformed training data set and the training class set; and
      (iii) storing, by the biomarker generator, when the first test class set and the second test class set differ, the second test class set as the first test class set and the transformed test data set as the test data set and returning to step (i); and
   (g) outputting, by the biomarker generator, when the first test class set is the same as the second test class set, the second test class set.

2. The method of claim 1, wherein the elements of the training data set represent gene expression data for a patient with a disease, for a patient resistant to the disease, or for a patient without the disease.

3. The method of claim 1, wherein the training data set is formed from a random subset of samples in an aggregate data set, and the test data set is formed from a remaining subset of samples in the aggregate data set.

4. The method of claim 1, wherein:
   the test data set includes a rest set of known labels, each known label identifying a class associated with each element in the test data set;
   the first test class set includes a set of predicted labels for the test data set; and
   the second test class set includes a set of predicted labels for the transformed test data set.

5. The method of claim 1, wherein the shifting at step (e) includes applying a rotation, a linear transformation, or a non-linear transformation to the training data set to obtain the transformed training data set.

6. The method of claim 1, wherein the shifting at step (i) includes applying a rotation, a shear, a linear transformation, or a nonlinear transformation to the test data set to obtain the transformed test data set.

7. The method of claim 1, further comprising:
   (h) comparing, by the biomarker generator, the first test class set to the second test class set for each of the plurality of iterations.

8. The method of claim 1, wherein the transforming at step (e) is performed by applying the same transformation of step (i).

9. The method of claim 1, further comprising:
   (h) providing, by the biomarker generator, the second test class set to a display device, a printing device, or a storing device.

10. The method of claim 1, wherein the first test class set and the second test class set differ if any element of the first test class set differs from a corresponding element of the second test class set.

11. The method of claim 1, wherein the second test class set includes a set of predicted labels for the transformed test data set, the method further comprising:
   evaluating, by the biomarker generator, the second classifier by computing a performance metric representative of a number of correct predicted labels in the second test class set divided by a total number of predicted labels.

12. The method of claim 1, wherein the first machine learning technique and the second machine learning technique are the same.

13. The method of claim 1, further comprising:
   (h) determining, by the biomarker generator, based on the second class set, a set of candidate biomarkers and at least one candidate error rate.

14. The method of claim 13, further comprising:
(i) receiving, by a biomarker consolidator in communication with the biomarker generator, the set of candidate biomarkers and the candidate error rate;
(j) determining, by the biomarker generator, a performance measure and size of each set of candidate biomarkers; and
(k) selecting, by the biomarker generator, based on the performance measure and size of each set of candidate biomarkers, an optimal biomarker.

15. The method of claim 13, further comprising:
(l) controlling, by a central control unit in communication with the biomarker generator and the biomarker consolidator, at least partially the operation of the biomarker generator and the biomarker consolidator.

16. A non-transitory computer-readable storage medium having instructions stored thereon that, when executed in a computerized system comprising at least one processor, cause said at least one processor to carry out operations, the operations comprising:
(a) receiving a training data set and a training class set, the training class set including a set of known labels, each known label identifying a class associated with each element in the training data set;
(b) receiving a test data set;
(c) generating a first classifier for the training data set by applying a first machine learning technique to the training data set and the training class set;
(d) generating a first test class set by classifying the elements in the test data set according to the first classifier;
(e) transforming the training data set by shifting the elements in the training data set by an amount corresponding to a center of a set of training class centroids, wherein each training class centroid is representative of a center of a subset of elements in the training data set;
(f) for each of a plurality of iterations:
(i) transforming the test data set by shifting the elements in the test data set by an amount corresponding to a center of a set of test class centroids, wherein each test class centroid is representative of a center of a subset of elements in the test data set
(ii) generating a second test class set by classifying the elements in the transformed test data set according to a second classifier, wherein the second classifier is generated by applying a second machine learning technique to the transformed training data set and the training class set; and
(iii) when the first test class set and the second test class set differ, storing the second test class set as the first test class set, storing the transformed test data set as the test data set, and returning to step (i); and
(g) outputting, when the first test class set is the same as the second test class set, the second test class set.

17. The non-transitory computer-readable storage medium of claim 16, the operations further comprising:
(h) outputting, when the first test class set and the second test class set do not differ, the second test class set.

18. The non-transitory computer-readable storage medium of claim 16, wherein the elements of the training data set represent gene expression data for a patient with a disease, for a patient resistant to the disease, or for a patient without the disease.

19. A computerized system comprising:
a biomarker generator; and
a memory coupled to the biomarker generator and having instructions stored thereon that, when executed, cause the biomarker generator to perform operations, the operations comprising:
(a) receiving a training data set and a training class set, the training class set including a set of known labels, each known label identifying a class associated with each element in the training data set;
(b) receiving a test data set;
(c) generating a first classifier for the training data set by applying a first machine learning technique to the training data set and the training class set;
(d) generating a first test class set by classifying the elements in the test data set according to the first classifier;
(e) transforming the training data set by shifting the elements in the training data set by an amount corresponding to a center of a set of training class centroids, wherein each training class centroid is representative of a center of a subset of elements in the training data set;
(f) for each of a plurality of iterations:
(i) transforming the test data set by shifting the elements in the test data set by an amount corresponding to a center of a set of test class centroids, wherein each test class centroid is representative of a center of a subset of elements in the test data set;
(ii) generating a second test class set by classifying the elements in the transformed test data set according to a second classifier, wherein the second classifier is generated by applying a second machine learning technique to the transformed training data set and the training class set; and
(iii) storing, when the first test class set and the second test class set differ, the second test class set as the first test class set and the transformed test data set as the test data set and returning to step (i); and
(g) outputting, when the first test class set is the same as the second test class set, the second test class set.

20. The computerized system of claim 19, the operations further comprising:
(h) outputting, when the first test class set and the second test class set do not differ, the second test class set.

21. The computerized system of claim 19, wherein the elements of the training data set represent gene expression data for a patient with a disease, for a patient resistant to the disease, or for a patient without the disease.

22. The computerized system of claim 19, wherein the training data set is formed from a random subset of samples in an aggregate data set, and the test data set is formed from a remaining subset of samples in the aggregate data set.

* * * * *